(12) United States Patent
Hutchinson et al.

(10) Patent No.: US 6,974,418 B1
(45) Date of Patent: Dec. 13, 2005

(54) AUTOMATIC CALIBRATION OF BLOOD VOLUME STATUS INDICATORS

(75) Inventors: George M. Hutchinson, Milwaukee, WI (US); Scott R. Wiese, Milwaukee, WI (US)

(73) Assignee: The General Electric Company, Schenectady, NY (US)

( * ) Notice: Subject to any disclaimer, the term of this patent is extended or adjusted under 35 U.S.C. 154(b) by 0 days.

(21) Appl. No.: 11/038,635

(22) Filed: Jan. 19, 2005

(51) Int. Cl.[7] ............................................. A61B 5/02
(52) U.S. Cl. .................... 600/481; 600/301; 600/485; 600/507
(58) Field of Search ........................................ 600/507

(56) References Cited

U.S. PATENT DOCUMENTS 5,048,532 A * 9/1991 Hickey ........................ 600/488

6,585,658 B2 * 7/2003 Redaelli et al. ............. 600/484

OTHER PUBLICATIONS

"The effect of the tidal volume and intravascular volume state on systolic pressure variation in ventilated dogs", A. Szold et al., Intensive Care Med (1989) vol. 15, pp. 368-371.

* cited by examiner

Primary Examiner—Robert L. Nasser
Assistant Examiner—Patricia C Mallari
(74) Attorney, Agent, or Firm—Andrus, Sceales, Starke & Sawall, LLP

(57) ABSTRACT

In a method for calibrating an indicator of the status of blood volume in a patient breathing with the aid of a mechanical ventilator, blood pressure data is obtained from the patient and used to determine a patient blood volume status indicator. Changes in at least one patient physiological characteristic or ventilator operating parameter are ascertained and used to alter the patient blood volume status indicator to provide a calibrated patient blood volume status indicator.

5 Claims, 3 Drawing Sheets

US 6,974,418 B1

AUTOMATIC CALIBRATION OF BLOOD VOLUME STATUS INDICATORS

BACKGROUND OF THE INVENTION

The present invention relates to a method for calibrating one or more patient blood volume status indicators derived from patient blood pressure data for changes in the latter arising from changes occurring in the mechanical ventilation of the patient.

In the ventilation of a patient with a mechanical ventilator, positive pressure breathing gases are supplied to the patient by the ventilator during inspiration. Expiration usually occurs from the natural relaxation action of the patient's thorax. The increase in intrathoracic pressure resulting from the expansion of the lungs by the positive pressure breathing gases causes changes in blood pressure measurements obtained from the patient. In general, an inspiratory intrathoracic pressure increase results in a decrease in arterial systolic and diastolic pressures that lags behind the intrathoracic pressure increase. This change is often termed the "respiratory swing," and is more pronounced under conditions of reduced blood volume in a patient, termed "hypovolemia" so that the extent of the changes in the cardiological data may be used to detect the state of, or changes in, patient blood volume. To this end, indicators such as the systolic blood pressure variation (SPV), the delta down component of SPV, or the variation in pulse pressure are employed. The "delta down" component of SPV is the difference between a minimal systolic value obtained during breathing and the minimal value obtained during a period of apnea (non-breathing state). For SPV, this indicator increases following a reduction in patient blood volume (hypovolemia) and decreases following an increase in patient blood volume (hypervolemia). U.S. Pat. No. 6,585,658 shows a method and system for automating patient blood volume status indicators obtained from cardiological patient data.

It is also known that when a patient is mechanically ventilated, changes in ventilation parameters or patient lung conditions will change the blood pressure data obtained from the patient causing changes to occur in the blood volume status indicator(s) derived from the blood pressure data. See, for example, *The Effect of Tidal Volume and Intravascular Volume State on Systolic Pressure Variation in Dogs*, R. Szold, et al., Intensive Care Med (1989), Vol. 15, pages 368 et seq. describing the effect of variation in tidal volume $V_T$ delivered by a ventilator on SPV and other patient blood volume status indicators.

In the past, it was common practice to carry out the mechanical ventilation using generally constant operating parameters for the ventilator. Depending on the patient treatment regimen, ventilator operating parameters typically include such parameters as the aforementioned tidal volume ($V_T$), as well as inspiratory pressure level (Pi), the ratio of the inspiratory time period to the expiratory time period (I:E ratio), the breath rate (BR), and the positive pressure maintained at the end of expiration (PEEP). As the ventilator settings were not changed, or only infrequently changed, in the course of a patient treatment, or among different patients, there was little loss in the clinical usefulness of the blood volume status indicator(s) obtained from the blood pressure data during ventilation of the patient. If ventilation settings were changed, clinicians would often attempt to estimate the effects of the changes on the blood volume status indicators in an effort to maintain the accuracy and usefulness of the indicators.

In more modern and sophisticated uses of mechanical ventilators, the operating parameters are more often varied over the course of a mechanical ventilation of a patient rather than remaining constant. This may be done, for example, in accordance with a sophisticated treatment regime for the patient, to promote weaning of the patient from the ventilator, or because conditions in the patient's lung, such as lung compliance, change. Lung compliance describes the relationship between the magnitude of a volume of breathing gas supplied to the patient's lungs and the magnitude of the resulting pressure produced in the lungs.

At present, however, as ventilator parameters or lung conditions change, resulting in changes in blood pressure data obtained from a patient, no effort is made to automatically calibrate or correct the blood pressure volume status indicators obtained from the blood pressure data. This means that, when such changes occur, an attending clinician will be provided with inaccurate information or information that is not on a uniform basis. As small changes in the indicators can represent significant changes in blood volume status, inaccurate information can mask important patient status changes and place the patient at risk.

SUMMARY OF THE PRESENT INVENTION

Briefly, the present invention is directed to a method for calibrating one or more indicators of the status of blood volume in a patient who is breathing with the aid of a mechanical ventilator. The calibration may be carried out automatically. In the method, blood pressure data is obtained from the patient and a patient blood volume status indicator such as SPV, the delta down component of SPV, or pulse pressure variation, is derived from the blood pressure data. One or more patient physiological characteristics, such as lung compliance or mechanical ventilator operating parameters such as those noted above, are also obtained. Changes in the patient physiological characteristic(s) or ventilating parameter(s) over time are ascertained. The patient blood volume status indicator is altered in accordance with changes in the patient physiological characteristic(s) or ventilating operating parameter(s) to provide a calibrated blood volume status indicator that accurately indicates the blood volume status of the patient.

BRIEF DESCRIPTION OF THE DRAWING

The present invention will be further appreciated from the following detailed description and accompanying drawing in which.

DETAILED DESCRIPTION OF THE PREFERRED EMBODIMENT(S)

Figure 1:
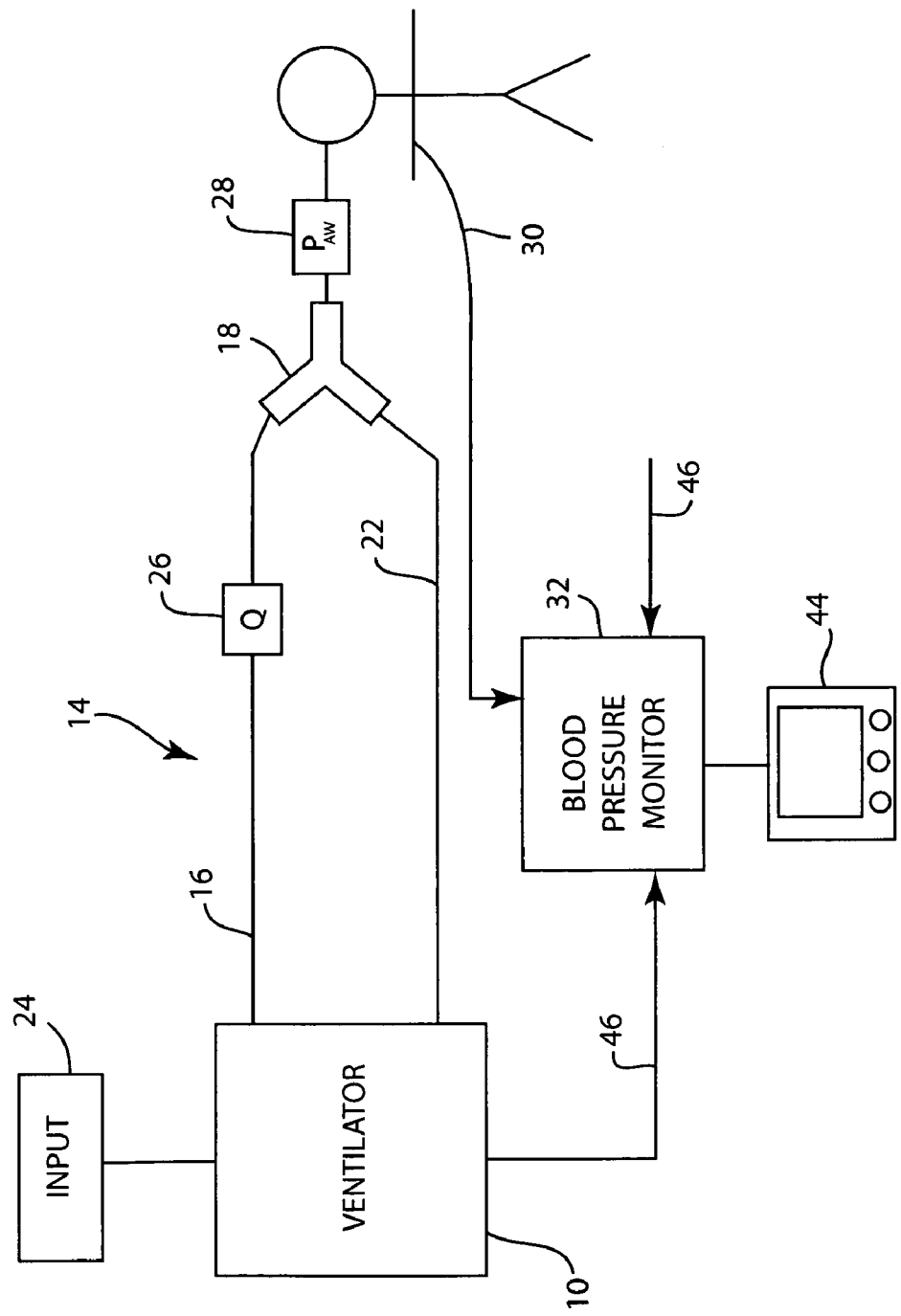
FIG. 1 is a general showing of apparatus suitable for carrying out the method of the present invention.

FIG. 1 shows apparatus for carrying out the method of the present invention. Ventilator 10 supplies breathing gases to patient 12 via breathing circuit 14. While the present invention is not so limited, FIG. 1 shows a breathing circuit 14 having an inspiratory limb 16, a wye connector 18, a patient limb 20, and an expiratory limb 22. Positive pressure breathing gases are provided from ventilator 10 through inspiratory limb 16, wye connector 18, and patient limb 20 to patient 12. Breathing gases exhaled by the patient pass through patient limb 20, wye connector 18, and expiratory limb 22. Ventilator 10 is provided with a user input 24 by which an attending the clinician sets the desired operating parameters for ventilator 10. Breathing circuit 14 may contain appropriate instrumentation, such as breathing gas flow sensor 26 and patient airway pressure sensor 28. Sensors 26 and 28 are connected to ventilator 10 for control and patient safety purposes.

Blood pressure data is obtained from patient 12. The blood pressure data may be obtained invasively as by placing an intravenous blood pressure sensing catheter 30 at an appropriate location in circulatory system of patient 12. It may also be obtained non-invasively as by auscultatory or oscillometric techniques. The blood pressure sensing means 30 is connected to blood pressure monitor 32.

Figure 2:
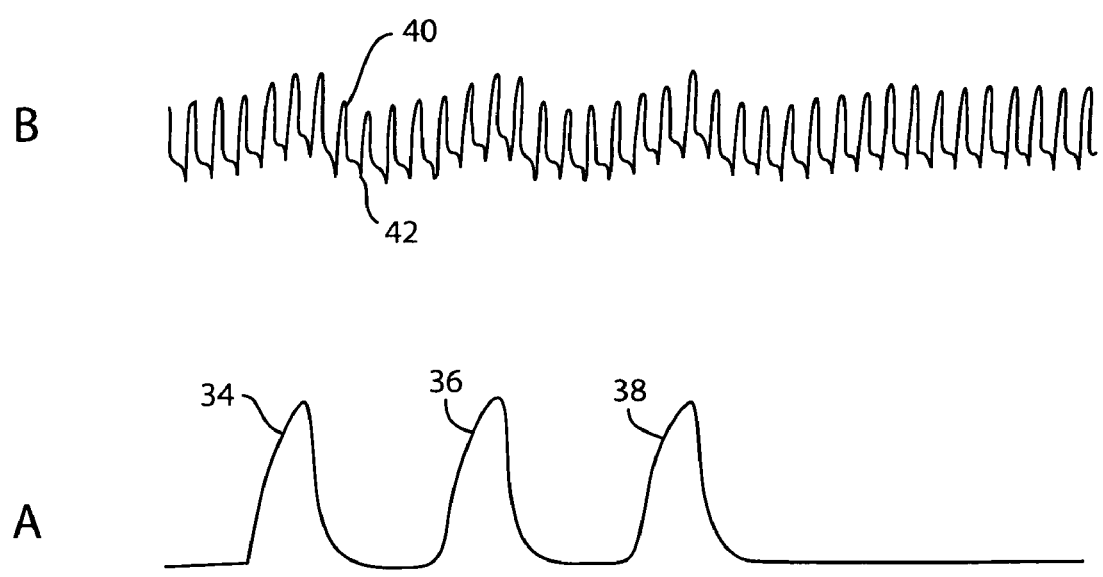
FIG. 2 is a graph showing breathing gas and blood pressure data for a patient.

FIG. 2 shows the relationship between blood pressure measurements obtained by blood catheter 30 and the ventilation of patient 12 by ventilator 10 as sensed by airway pressure sensor 28. As described above, following each supply of positive pressure breathing gases in breaths 34, 36, 38, shown in graph FIG. 2A, there is a decrease in the arterial systolic and diastolic pressures 40 and 42, respectively, that lags behind the positive pressure breathing gases. The difference between the systolic blood pressure during a breath and following a breath forms the systolic pressure variation (SPV) and changes in this quantity may be used to detect the state of, or changes in, patient blood volume. The right hand side of FIG. 2 shows a period of non-breathing, or apnea. The delta down component of SPV can be determined by examining difference between the minimal systolic blood pressure obtained during the breathing shown at the left had side of FIG. 2 and that obtained during apnea shown on the right hand side.

Blood pressure monitor 32 determines one or more desired patient blood volume status indicators from the blood pressure data and provides same in graphic or numerical form in display 44.

To carry out the method of the present invention, ventilator 10 is connected to blood pressure monitor 32 by a link, illustrative shown as conductor 46, so that signals indicative of changes in the operating parameters of ventilator 10 may be provided to blood pressure monitor 32. Signals indicative of changes in a physiological condition of patient 12 may also be provided in conductor 46. For example, patient lung compliance can be determined using sensors 26 and 28 connected to ventilator 10. Or, changes in a physiological condition of a patient can be inputted through a separate monitoring means (not shown) to blood pressure monitor 32 via conductor 46.

Figure 3:
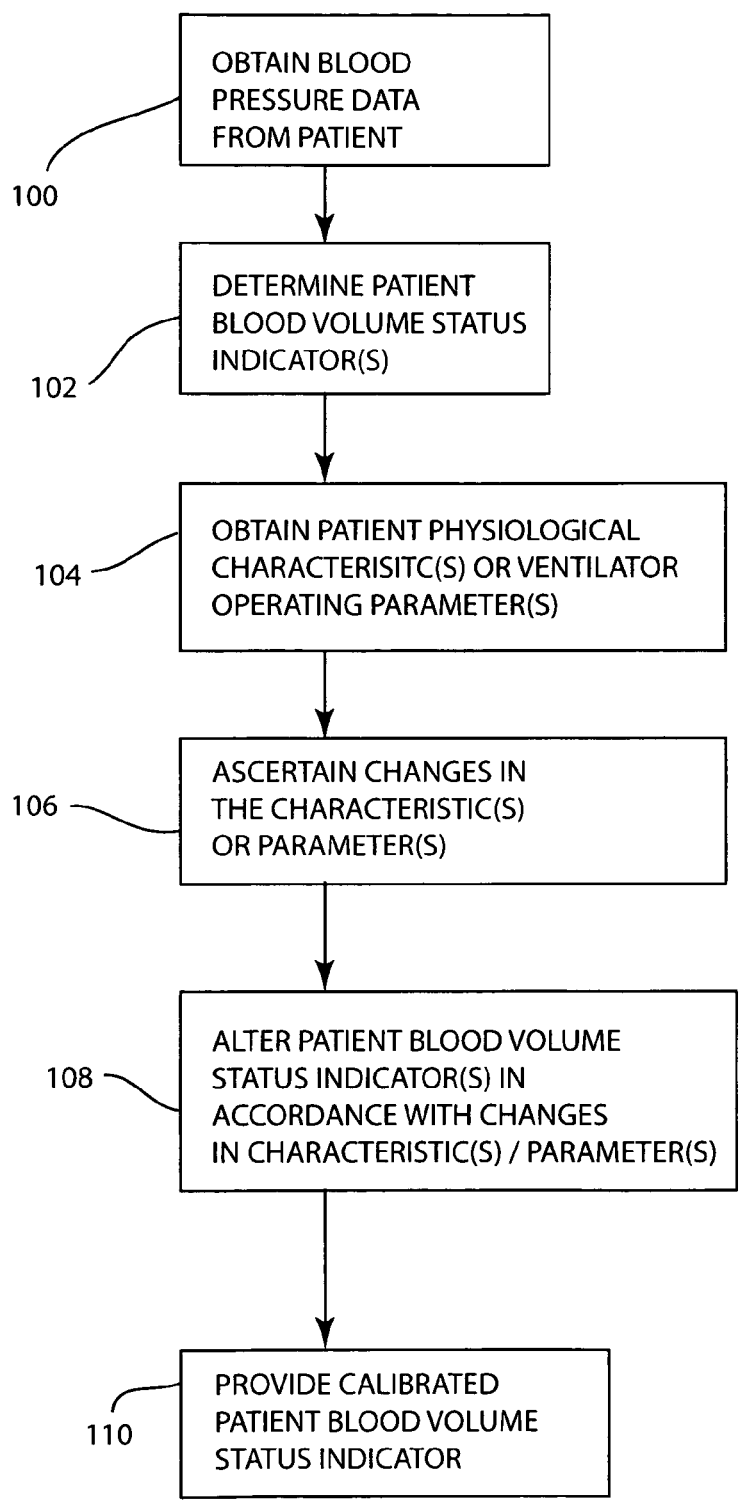
FIG. 3 is a flow chart showing the steps of the method of the present invention.

FIG. 3 is a flow chart indicating the steps of the method of the present invention. In step 100, blood pressure data is obtained from patient 12, as by blood pressure catheter 30. In step 102, the blood pressure data is used to determine a patient blood volume status indicators. Such indicators include but are not limited to the systolic blood pressure variation (SPV), the delta down component of SPV, and pulse pressure variation.

In step 104, one or more patient physiological characteristics, such as lung compliance, or one or more ventilator operating parameters are obtained as from ventilator 10 or other monitoring device. As noted above, operating parameters of the ventilator deemed suitable for use in the present invention include, but are not limited to, tidal volume, inspiratory pressure level, I:E ratio, breath rate, and PEEP.

In step 106, as the ventilation of patient 12 proceeds, changes in the patient physiological characteristic(s) or ventilator operating parameter(s) are determined and provided to blood pressure monitor 32 in conductor 46.

It will be appreciated that while changes in at least one of a patient characteristic or operating parameter must be provided to blood pressure monitor 32 to carry out the method of the present invention, in a practical embodiment of the present invention, data reflecting changes in several or all of the characteristics or parameters will be provided to blood pressure monitor 32.

In step 108, the patient blood volume status indicator(s) are altered in accordance with changes in the patient physiological characteristic(s) and/or ventilator operating parameter(s) to provide a calibrated or corrected blood volume status indicator to display 44 in step 110. An example of such an alteration is as follows. Assume there are no changes in blood volume occurring in patient 12. An increase in the tidal volume $V_T$ supplied to patient 12 by ventilator 10 will increase the systolic blood pressure variation SPV in the blood pressure data obtained from blood pressure catheter 30. This increase in the SPV would ordinarily be taken as indicative of a decrease in the blood volume of the patient when, in fact, no such decrease has occurred.

To avoid an erroneous indication of a blood volume status change when the tidal volume to patient 12 is increased, in accordance with the present invention, in step 108, the SPV patient blood volume status indicator obtained from the blood pressure data from patient 12 is reduced by an amount necessary to compensate for any increases caused by the increase in the tidal volume of breathing gases supplied to patient 12 by ventilator 10. The calibrated indicator(s) provided to display 44 would remain the same to avoid an erroneous indication of a change in patient blood volume status.

In a corresponding manner, compensation would be provided to the patient blood volume status indicator(s) obtained from the blood pressure data for changes in other operating parameters of ventilator 10 or for changes in patient physiological characteristics.

While a specific embodiment of the invention is set out above, it will be appreciated that the invention is not limited to the foregoing exemplary description. Rather, various alternatives and embodiments are contemplated as being within the scope of the following claims particularly pointing out and distinctly claiming the subject matter regarded as the invention.

What is claimed is:

1. A method for calibrating an indicator of the status of blood volume in a patient breathing with the aid of a mechanical ventilator, the blood volume status indicator being derived from blood pressure measurements carried out on the patient, the physiological characteristics of the patient's lungs being subject to change and the operating parameters of the mechanical ventilator being alterable during ventilation, said method comprising the steps of:
   a) obtaining blood pressure data from the patient;
   b) determining a patient blood volume status indicator from the blood pressure data;
   c) obtaining at least one patient physiological characteristic or mechanical ventilator operating parameter;
   d) ascertaining changes in the at least one patient physiological characteristic or ventilator operating parameter;
   e) altering the patient blood volume status indicator in accordance with changes in the at least one patient physiological characteristic or ventilator operating parameter; and
   f) providing a calibrated patient blood volume status indicator.

2. The method according to claim 1 wherein step (a) comprises obtaining at least one of systolic and diastolic blood pressure values from the patient.

3. The method according to claim 2 wherein step (b) comprises determining a patient blood volume status indicator based on at least one of systolic pressure variation, delta down, and pulse pressure variation.

4. The method according to claim 1 wherein step (c) is further defined as obtaining a patient physiological characteristic comprising lung compliance.

5. The method according to claim 1 wherein step (c) is further defined as obtaining a mechanical ventilator operating parameter comprising at least one of tidal volume, inspiratory pressure level, inspiratory:expiratory ratio, and positive end expiratory pressure.

* * * * *